United States Patent
Filanovsky (10) Patent No.: US 7,244,345 B1
(45) Date of Patent: Jul. 17, 2007

(54) ELECTROCHEMICAL METHOD AND SENSOR FOR THE DETECTION OF TRACES OF EXPLOSIVES

(75) Inventor: Boris Filanovsky, Jerusalem (IL)

(73) Assignee: Medis Technologies Ltd., Yahud (IL)

( * ) Notice: Subject to any disclaimer, the term of this patent is extended or adjusted under 35 U.S.C. 154(b) by 231 days.

(21) Appl. No.: 10/715,489

(22) Filed: Nov. 19, 2003

(51) Int. Cl.
*G01N 27/403* (2006.01)

(52) U.S. Cl. .................. 204/402; 204/409; 205/780.5

(58) Field of Classification Search .............. 204/400, 204/402, 409, 411; 205/780.5
See application file for complete search history.

(56) References Cited

U.S. PATENT DOCUMENTS

| | | | |
|---|---|---|---|
| 4,696,184 A * | 9/1987 | Fukumoto et al. ......... 73/32 R |
| 4,895,620 A * | 1/1990 | Ko et al. ................. 162/138 |
| 4,970,145 A * | 11/1990 | Bennetto et al. ....... 204/403.11 |
| 4,987,767 A | 1/1991 | Corrigan et al. |
| 5,120,421 A | 6/1992 | Glass et al. |
| 5,296,125 A | 3/1994 | Glass et al. |
| 5,521,101 A | 5/1996 | Saini et al. |
| 5,762,808 A * | 6/1998 | Peyton ....................... 210/748 |
| 6,356,433 B1 * | 3/2002 | Shi et al. ................... 361/502 |
| 6,477,907 B1 | 11/2002 | Chambers et al. |
| 6,562,497 B2 | 5/2003 | Finkelshtain et al. |
| 6,571,649 B2 | 6/2003 | Sakairi et al. |
| 6,573,107 B1 | 6/2003 | Bowen et al. |

OTHER PUBLICATIONS

Naal et al, Analytical Chemistry, 2002, 74, pp. 140-148.*
Xu et al, Analyst, 2000, 125, pp. 1453-1457.*
Ye et al, Analytical Chemistry, 1988, 60, pp. 1979-1982.*
CAPLUS abstract for US Patent 4,696,184.*
Niu et al, Journal of Electroanalytical Chemistry 546, 2003, pp. 59-72.*
Malinauskas et al, Journal of Electroanalytical Chemistry 484, 2000, pp. 55-63. □□*
STN Registry for Toluidine Blue, Nov. 1984.*
Levi et al, Electrochimica Acta, 38, 1993, pp. 271-279.*
CAPLUS record for Kitani et al, Molecular Crystals and Liquid Crystals, 296, 1997, pp. 349-356.*
"Comparison of Cabron Electrode Bulk modified with HgJ2 and GC Electrode Surface modified with HgJ2 as C/Hg electrode" Filansky; Reviews in Anal. Chem. V18, No. 5 (1999) pp. 293-299, month unknown.
"Explosives Detection Systems (EDS) for Aviation Security" Singh et al;Signal Processing 83 (2003) pp. 31-55, month unknown.
"Single-Channel Microship For Fast Screening And Detailed Identification Of Nitroaromatic Explosives Or Organophosphate Nerve Agents" Wang et al; Anal Chem 2002, 74 pp. 1187-1191, month unknown.

(Continued)

*Primary Examiner*—Kaj K. Olsen
(74) *Attorney, Agent, or Firm*—Mark M. Friedman (57) ABSTRACT

A system for highly sensitive electrochemical detection of trace nitro-aromatic compounds in air, uses a carbon or carbon/gold working electrode with a surface that is modified to increase the electron transfer kinetics of nitro-aromatic compounds. Chemical modifiers of the working electrode surface include amino-aromatic compounds such as aniline and its derivatives. The detection method involves dissolving trace nitro-aromatic compounds in an electrolyte including aprotonic solvents, or dipolar solvents, in the electrochemical cell including a working electrode, a reference electrode and an auxiliary electrode. Voltage is varied across the working electrode and the reference electrode, and an electrical current is measured between the working electrode and the auxiliary electrode. The measured electrical peak current is a sensitive indication of the concentration of the trace compounds. This invention is appropriate for portable, field-testing of trace explosive compounds in air.

18 Claims, 6 Drawing Sheets

OTHER PUBLICATIONS

"Remote electrochemical sensor for monitoring TNT in natural waters" Wang et al; Analytica Chimica Acta 361 (1998) 85-91, month unknown.

"On-Line Electrochemical Monitoring Of (TNT) 24,6-Trinitrotoluene In Natural Waters" Wang et al; Analytica Chimica Acta pp. 139-144, month unknown.

"Screen-printed voltammetric sensor for TNT" Wang et al; Talanta 46 (1998) pp. 1405-1407, month unknown.

"Electrochemical Response Of New Carbon Electrodes Bulk Modified With Cobalt Phthalocyanine To Some Thiols In The Presence Of Heptane Or Human Urine" Filanovsky; Alanlytic Chimica Acta 394 (1999) 91-100, month unknown.

* cited by examiner

ELECTROCHEMICAL METHOD AND SENSOR FOR THE DETECTION OF TRACES OF EXPLOSIVES

FIELD OF THE INVENTION

The present invention relates to the detection of trace amounts of explosive materials such as nitro-aromatic compounds in air, using an electrochemical measurement technique, and specifically to improving the sensitivity of the measurement of trace explosive materials, and decreasing measurement time. More specifically, the present invention relates to a method of explosives detection of low cost that is suitable for portable field-testing.

BACKGROUND OF THE INVENTION

As a consequence of recent efforts to thwart the recent upsurge in international terrorism, there is an increased interest in the detection of explosive materials. These materials include nitro-aromatic compounds including 2,4,6-trinitrotoluene (TNT), dinitrotoluene (DNT) and similar derivatives.

Many detection methods have been used to detect explosive materials. These methods include gas and HPLC chromatography, x-ray scattering, neutron analysis, nuclear quadrupole resonance, and mass spectrometry (U.S. Pat. No. 6,571,649). These methods generally require expensive and sophisticated equipment, (e.g. high vacuum), equipment that is not portable (e.g. cylinders of compressed gases), and/or have a complicated sample preparation. These techniques, are therefore, not appropriate for low cost portable field-testing for trace explosive materials. A recent review of some of these methods for explosives detection is "Explosives detection systems (EDS) for aviation security" (Singh, S., Signal Processing vol. 83, 2003, p. 31-55).

Another known method for the detection of trace amounts of explosive materials utilizes immunochemical sensors. For example, U.S. Pat. No. 6,573,107 is directed towards the immunochemical detection of explosive substances in the gas phase using surface plasmon resonance spectroscopy. Immunochemical detection methods potentially offer high selectivity and high sensitivity.

Electrochemical detection refers to the use of electrodes, immersed in an electrolyte, and connected to an instrument that varies the voltage applied to the electrodes. The instrument measures the current flow between the electrodes. Typically, the electrode potential is varied; and an electric current flows between the electrodes that is characteristic of the presence of electrochemical active substances in the electrolyte. The magnitude of the current is proportional to the concentration of the electrochemical active substances. It is well known that TNT and other nitro-aromatic compounds are reduced electrochemically at the cathode and may be detected by electrochemical detection. Wang et. al. (Analytica Chimica Acta, vol. 485 (2003) p. 139-144) reported the monitoring of TNT in natural waters using an electrochemical technique. They reported a measurement sensitivity of 0.003 µA/ppb of TNT in natural seawater. This sensitivity level was achieved by Wang et. al. by subtracting the background signal, in natural seawater not contaminated by TNT, caused by the reduction of dissolved oxygen. The applicant reported (Reviews Analytical Chemistry vol. 18 no. 5, 1999, p. 293) the use of carbon/Hg film electrode materials in an aqueous solvent. This electrode material was successful to minimize the background by separating the atmospheric $O_2$ background current from the TNT current, however the sensitivity reported was only ~0.7 µA/µM (~0.003 µA/ppb) and was comparable to the sensitivity reported by Wang. Despite these positive developments in the prior art, the sensitivity is still insufficient, and the kinetics of the TNT reduction reaction are too slow to achieve a practical portable field test for trace explosive materials. A practical electrochemical sensor for trace explosive materials should have high sensitivity, a short measurement time and in addition a way of cleaning the electrodes rapidly to perform further testing.

There is thus a widely recognized need for an electrochemical method and sensor for the detection of traces of explosives, and it would be highly advantageous to have an electrochemical method and sensor for the detection of traces of explosives, with high sensitivity, and fast reaction kinetics.

SUMMARY OF THE INVENTION

According to the present invention, there is provided a system for electrochemical assay of nitro-aromatic compounds, including: (a) a working electrode having a surface modified with a chemical that increases electron transfer kinetics of the nitro-aromatic compounds.

Preferably, the chemical that increases the electron transfer kinetics is an aromatic compound, for example an amino-aromatic compound, an alkyl-aniline compound, a halide derivative of an alkyl aniline compound and/or an hydroxyl-aniline compound. Most preferably, the chemical modifier is phenylene-diamine, diphenylene-diamine, diphenylene-triamine, or aniline.

Preferably, the working electrode contains elemental carbon or gold; the working electrode includes submicron particles and the elemental gold is a coating on the electrode surface. Preferably, the working electrode includes carbon paper.

Preferably, the system includes in addition, (b) an electrolyte for dissolving the nitro-aromatic compounds, and the electrolyte is chosen to minimize background current resulting from oxygen reduction.

Preferably, the electrolyte includes an aprotonic solvents, and/or dipolar solvents; such as dimethylformamide, acetonitrile, propylene carbonate and optionally also a solvent such as ethanol, propanol, ethylene-glycol, and/or propylene-glycol.

Preferably, the system further includes (c) a mechanism for inputting air suspected to include the nitro-aromatic compounds, into the electrolyte in order to dissolve the nitro-aromatic compounds in the electrolyte.

According to the present invention, there is provided an electrochemical method of assaying trace compounds in air, including the steps of (a) dissolving the trace compounds in an electrolyte that includes aprotonic solvents, and/or dipolar solvents; (b) immersing a working electrode in the electrolyte; (c) applying a varying potential to the working electrode; and (d) measuring an electrical current consequent to the varying potential, thereby providing measurement results indicative of a concentration of the trace compounds.

Preferably, after measurement, the electrochemical method includes (e) regenerating the working electrode by applying a negative potential to the working electrode.

Preferably, the dissolving of trace compounds is performed by bubbling air containing the trace compounds through the electrolyte.

Preferably, the electrochemical method includes, prior to dissolving the trace compounds in the electrolyte, the steps of: (f) measuring a background electrical current, while applying a varying potential, thereby obtaining background current results; and (g) subtracting the background current results from the measurement results, thereby obtaining calibrated measurement results.

Preferably, the electrolyte used in the electrochemical method includes dimethylformamide, acetonitrile, and/or propylene carbonate; optionally also ethanol, propanol, ethylene-glycol, and/or propylene-glycol and preferably the electrolyte has pH greater than 7. Preferably, the electrochemical method includes preconditioning the working electrode thereby increasing electron transfer kinetics of the trace compounds. The preconditioning modifies the working electrode with a chemical such as amino-aromatic compounds, alkyl-aniline compounds, halide derivatives of alkyl aniline compounds and/or hydroxyl-aniline compounds. According to the present invention, there is provided an electrochemical method of assaying nitro-aromatic compounds in air, including the steps of: (a) dissolving the nitro-aromatic compounds in an electrolyte that includes an aprotic solvent, and/or a dipolar solvent; (b) immersing a working electrode in the electrolyte; (c) applying a varying potential to the working electrode; (d) measuring an electrical current consequent to the varying potential, thereby providing measurement results, indicative of a concentration of the nitro-aromatic compounds.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is an electrochemical method and sensor for the detection of traces of explosives. Specifically, the present invention can be used for the detection of trace amounts in air of nitro-aromatic compounds including 2,4, 6-trinitrotoluene (TNT), dinitrotoluene (DNT) and similar derivatives.

The principles and operation of an electrochemical method and sensor for the detection of traces of explosives, according to the present invention, may be better understood with reference to the drawings and the accompanying description.

Figure 1:
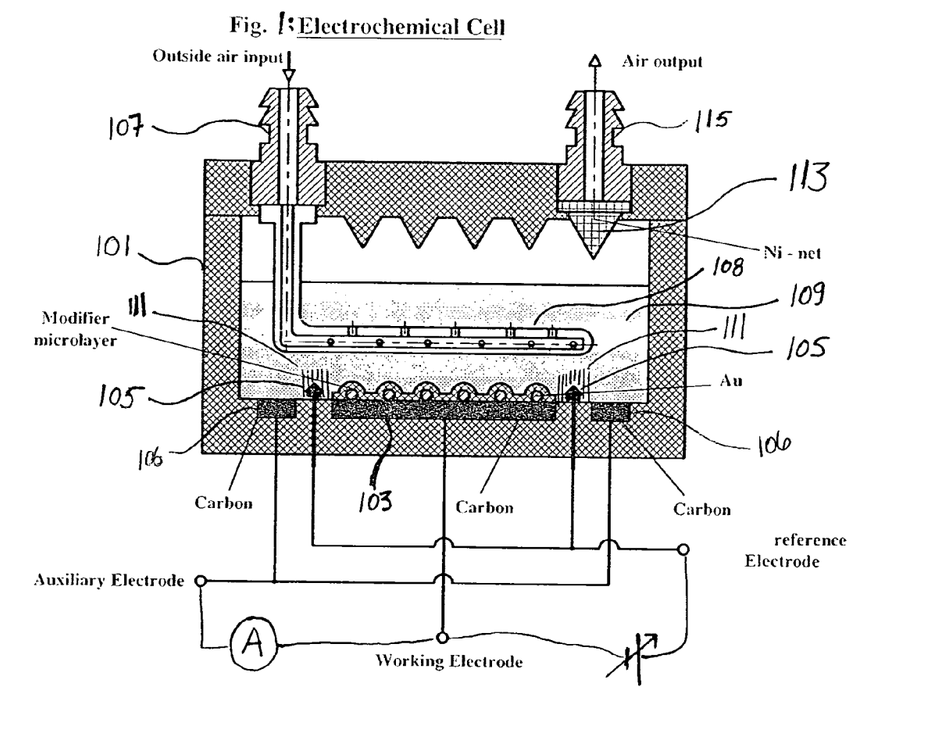
FIG. 1 is a drawing of an electrochemical cell used to sense trace explosive materials, according to the present invention.

Referring now to the drawings, FIG. 1 illustrates an electrochemical cell 101 including a working electrode 103, a reference electrode 105, an auxiliary electrode 106, an electrolyte 109, an air inlet 107 that passes air into the cell through a perforated tube 108 allowing air to bubble through electrolyte 109, and an air outlet 115 that lets air out of the cell. Reference electrode 105 is an Hg/HgCl electrode that includes an element 111 to protect reference electrode 105 from air bubbles. Electrolyte 109 is a solvent or a mixture of solvents including trace materials dissolved in the solvent(s). These trace materials, including nitro-aromatic compounds dissolved in the solvent(s), are admitted to the solvent mixture from the air using air inlet 107 and dissolved in electrolyte 109 by bubbling the air through electrolyte 109. Air is output through air outlet 115. A metal screen 113 is used to prevent electrolyte 109 from escaping through air outlet 115. Voltage is applied between working electrode 103 and reference electrode 105. A current is measured which flows between reference electrode 103 and auxiliary electrode 106, as a result of oxidation-reduction reactions on the electrode surfaces in electrolyte 109.

Working electrode 103 is prepared by a technique of galvanic Au planting of carbon on an ordinary carbon paper surface in an aqueous solution of $HAuCl$, $K_4Fe(CN)_6$, and $Na_2CO_3$ at current density 1 ma/cm$^2$. The carbon particles are of typical dimension 0.1-1 µm. The carbon paper with density 0.4-0.8 g/cc, part number P2 or P3 was supplied by E-TEK Inc. (Somerset, N.J., USA). The gold deposited on the carbon particles is of approximate average thickness, 0.30-0.60 nm. All reagents used were obtained from Sigma-Aldrich (USA).

Voltammetric measurements were performed using a CV-50W potentiostat of Bioanalytical Systems Inc. (West Lafayette, Ind., USA). Measurements were performed in the differential pulse (DIP) mode. A background current was measured using background electrolyte 109 before trace elements are introduced into electrolyte 109. Trace elements are then introduced into electrolyte 109 through air inlet 107 using a standard air pump (not shown in FIG. 1) with throughput 1500 ml/min for 20 sec. The current measurement is then performed and the background current is subtracted from the measured current to yield the measured results. The potential range is from −150 mV to −500 mV; the scan rate is from 30 to 50 mV/sec. Electrochemical active substances in the air including nitro-aromatic compounds (e.g. TNT) are dissolved in electrolyte 109 and are detected electrochemically.

Figure 2:
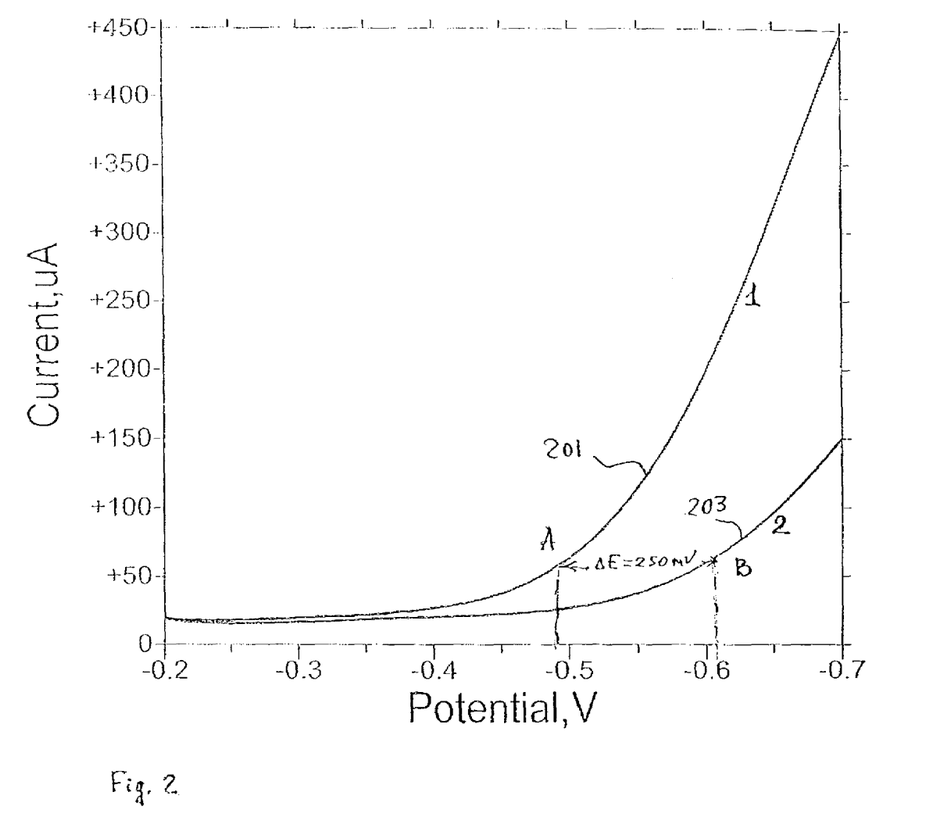
FIG. 2 is a graph of background current measured in an electrochemical cell using both a conventional aqueous solvent and an electrolyte of the present invention.

FIG. 2 is a graph of DIP voltammetric data measured with C/Au working electrode 103. For data trace 201, electrolyte 109 is 0.1M $KClO_4$ in water with pH 9.0. For data trace 203, electrolyte 109 is 0.1M $KClO_4$ in a mixture of water, ethanol, and acetonitrile (1:1:1 v/v), with pH 9.0. FIG. 2 shows a window of about 250 mV, between potentials −0.5 and −0.6V where trace 302 has a lower background current. The higher background current of trace 201 is attributed to dissolved gaseous oxygen that interferes with the measurement. Consequently, the mixed electrolyte of trace 203 is preferred.

Figure 3:
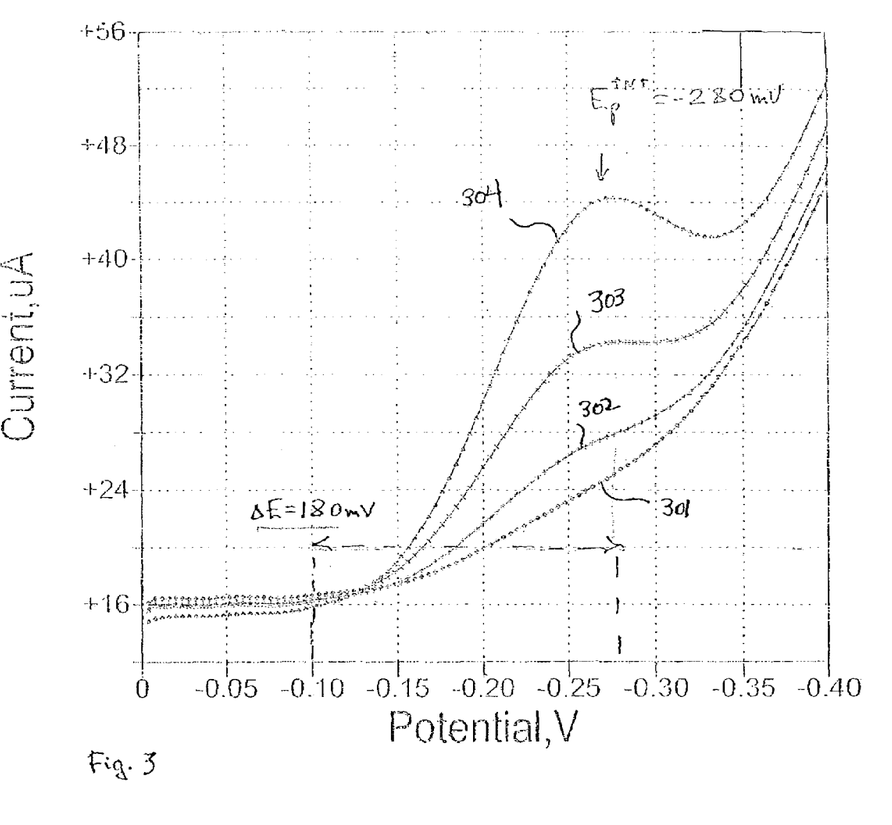
FIG. 3 is a graph showing the sensitivity of the TNT detection, using an electrolyte of the present invention, and a conventional working electrode.

FIG. 3 is a graph of DIP voltammetric data measured using an electrochemical cell shown in FIG. 1, according to the present invention. However, the data of FIG. 3 were measured with a working electrode C/Au 103 that was immersed in pure dimethylsulfoxide (DMSO) for 5 minutes at room temperature. Trace 301 is the background voltammetric data with electrolyte 109 of pH 4 consisting of water/ethanol/acetonitrile 1:1:1 (v/v). Trace 302 shows the voltammetric data with 200 ug/l (200 ppb) TNT dissolved in electrolyte 109. Each subsequent trace 302 to 304 shows voltammetric data each with an additional 200 ug/l (200 ppb) TNT dissolved in electrolyte 109. The TNT measurement sensitivity is 0.003 µA/ppb.

Figures 3A, 4:
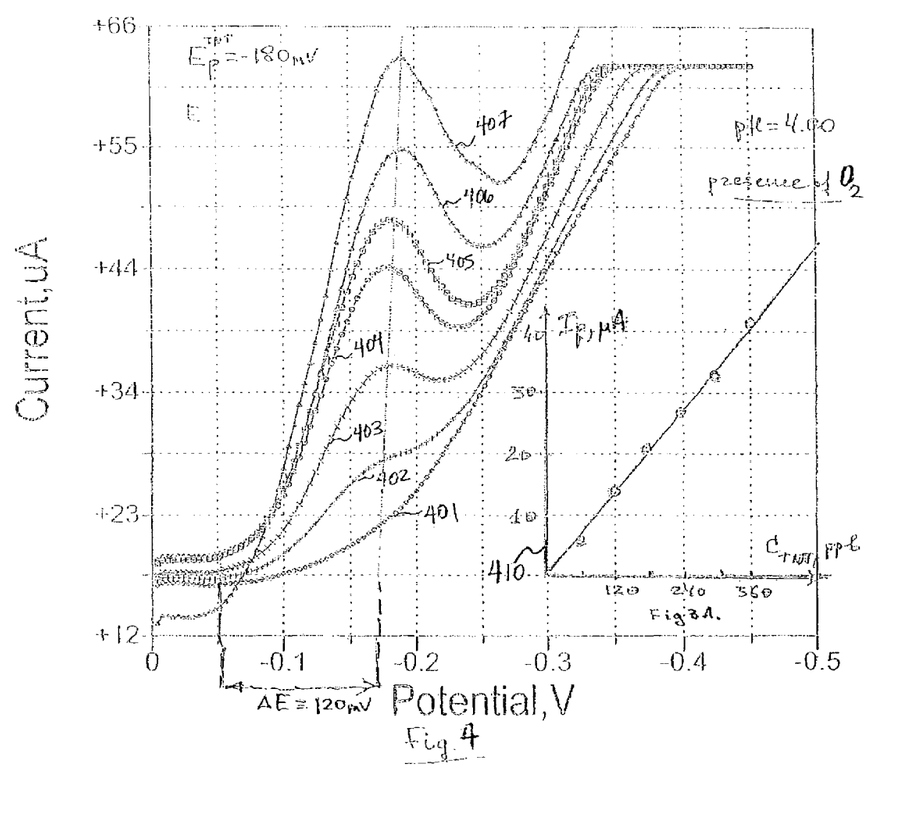
FIG. 4 is a graph showing the measurement sensitivity at pH=4 with a modified electrode, according to the present invention.

FIG. 4 is a graph of DIP voltammetric data measured in accordance with the present invention. Working electrode 103 is preconditioned by immersing working electrode 103 in a 2% solution of aniline in DMSO for 5 minutes at room temperature. Electrolyte 109 is the same as that of FIG. 3, of pH 4, consisting of water/ethanol/acetonitrile 1:1:1 (v/v). Trace 401 shows the background voltammetric data. Each subsequent trace 402 to 407 shows voltammetric data each with an additional 60 µg/l (60 ppb) TNT dissolved in electrolyte 109. The sensitivity of the measurement is shown in the graph of inset 410, in which the abscissa is the TNT concentration (ppb) and the ordinate is the measured peak current in µA. The measured sensitivity is 0.11 µA/ppb. These data compared with the data of FIG. 3 show that the surface modification of working electrode 103 with aniline significantly improves the measurement sensitivity of TNT.

Figure 5:
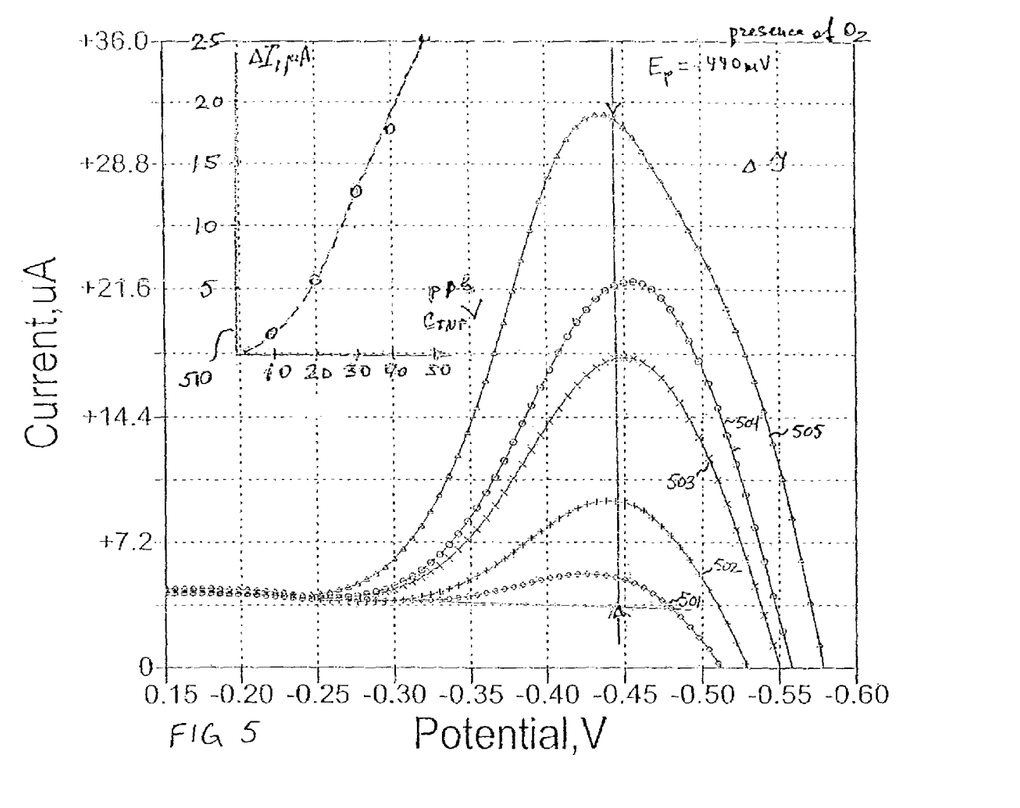
FIG. 5 is a graph showing the measurement sensitivity with a modified electrode and with electrolyte of pH=9, according to the present invention.

FIG. 5 is a graph of DIP voltammetric data measured in accordance with the present invention. The surface of working electrode 103 is immersed as in the measurement of FIG. 4, in a 2% solution of aniline in DMSO. Electrolyte 109 is similar to that used in the measurement of FIG. 4, consisting of water/ethanol/acetonitrile 1:1:1 (v/v), but with pH 9. The pH was achieved using Merck buffer capsules, no. CPM90L4 pH=9. Traces 501 to 505 show the calibrated data after subtracting the background data. Traces 501 to 505 show the calibrated data each with an additional 10 µg/l (10 ppb) dissolved in electrolyte 109, starting with 10 µg/l in trace 501. Graph inset 510 shows a sensitivity of 0.50 µA/ppb. These data compared with the measurement of FIG. 4 show that the high pH increases the measurement sensitivity.

Figures 5A, 6:
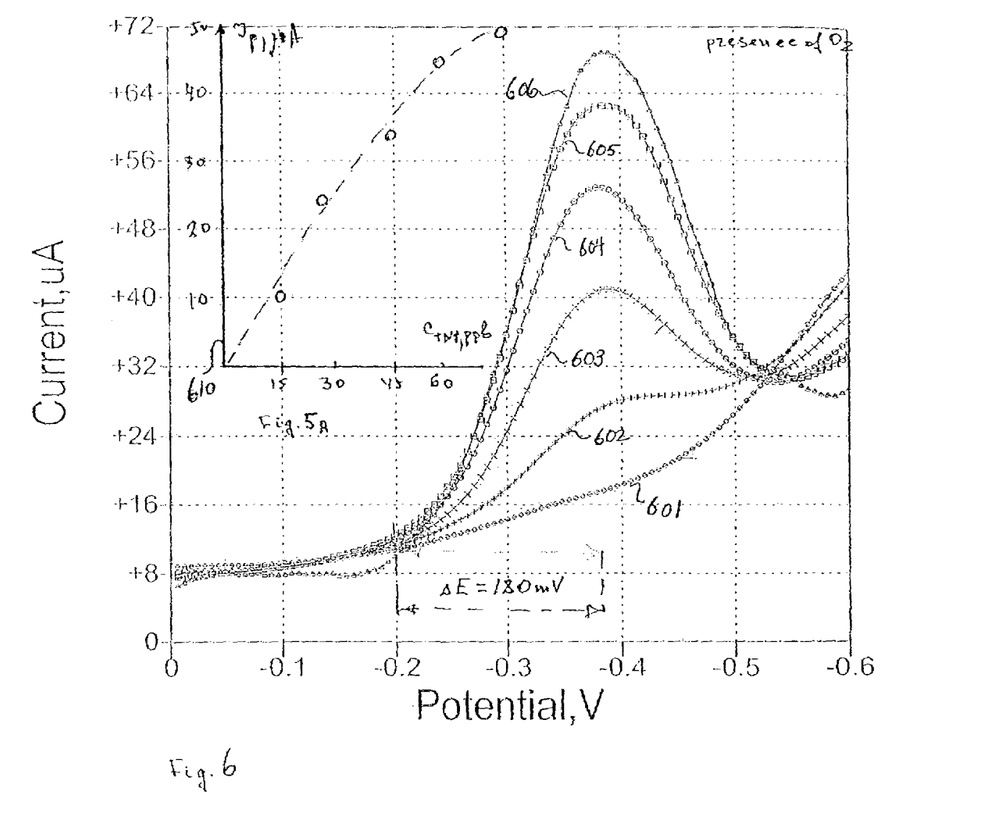
FIG. 6 is a graph showing the measurement sensitivity with an electrode surface further modified according to the present invention.

FIG. 6 is a graph of DIP voltammetric data measured in accordance with the present invention. The surface of working electrode 103 is preconditioned by immersing working electrode 103 in a 3% solution of aniline in DMSO for 5 minutes at room temperature. Electrolyte 109 is the same as that of the measurement of FIG. 5, consisting of water/ethanol/acetonitrile 1:1:1 (v/v), with pH 9. Trace 601 shows the background data. Traces 602 to 606 show the measured data without subtracting the background data. Traces 602 to 606 show the measured data, each when an additional 15 ppb of TNT is dissolved in electrolyte 109, starting with 15 ppb of TNT in trace 602. The measured sensitivity is shown in graph inset 610. The measured sensitivity is 0.66 µA/ppb, showing that the stronger aniline treatment significantly improves the sensitivity.

The measurement of nitro-aromatic compounds, according to the present invention requires about 30-40 sec. After the detection of nitro-aromatic compounds, working electrode 103 is regenerated, if necessary, using a high negative potential about −1000 to −1300 mV. Regeneration time is about 5 seconds. Therefore, the electrochemical technique, according to the present invention, is suitable for rapid and portable field-testing of nitro-aromatic compounds. The experimental results show that the use of solvents which are aprotonic, organic dipolar, or have a high dielectric constant, as part of electrolyte 109, are expected to improve the detection sensitivity, according to the present invention. These solvents include acetonitrile, dimethyl-formamide and propylene-carbonate and mixtures thereof. Other polar solvents such as ethanol, propanol, ethylene-glycol, and propylene-glycol may be added as diluents. A preferred diluent has a high boiling point and is stable against evaporation. The electrode used, according to the present invention, is manufactured from ordinary carbon paper. Carbon paper is readily available, of low cost and therefore suitable for a disposable electrode. An electrode, including a carbon particle layer on other substrates including cloth or glass, will function in a similar way.

The experimental results furthermore show that the chemical modification of a, carbon or carbon/gold electrode, with compounds similar to aniline, preconditions the electrode surface to increase the sensitivity of the measurement, according to the present invention. These compounds include aromatic compounds containing amino groups, including derivatives that are mono-alkyl (e.g. methyl, ethyl, propyl, . . . ), di-alkyl or tri-alkyl. The chemical modifiers, according to the present invention include aromatic-aniline compounds such as, phenylene-diamine, diphenylene-diamine, diphenylene-triamine and similar compounds and derivatives. This chemical modification is necessary because the reduction of nitro-aromatic compounds has slow kinetics. The modification successfully increases the electron transfer rate from the solution to electrode 103 and therefore increases the sensitivity of the measurement and lowers the detection limit. Other modifiers that increase electron transfer, according to the present invention, include compounds such as J. Meisenheimers complexes, known to mediate electron transfer, and other nitro-amine complexes; and alkyl-aniline and its derivatives; and halide derivatives of alkyl aniline compounds as well as hydroxyl-aniline compounds.

While the invention has been described with respect to a limited number of embodiments, it will be appreciated that many variations, modifications, and other applications of the invention may be made.

What is claimed is:

1. A system for electrochemical assay of nitro-aromatic compounds, comprising:
   (a) a working electrode having a surface of carbon and gold, wherein said surface is modified by a monomeric amino-aromatic compound by treatment thereof with said monomeric amino-aromatic compound dissolved in an organic polar solvent.

2. The system, according to claim 1 wherein said monomeric amino-aromatic compound is selected from the group consisting of alkyl-aniline compounds, halide derivatives of alkyl-aniline compounds and hydroxyl-aniline compounds.

3. The system, according to claim 1, wherein said monomeric amino-aromatic compound is selected from the group consisting of phenylene-diamine, diphenylene-diamine, and diphenylene-triamine.

4. The system, according to claim 1, wherein said monomeric amino-aromatic compound is aniline.

5. The system, according to claim 1, wherein said organic polar solvent is a polar aprotonic solvent.

6. The system, according to claim 1, wherein said organic polar solvent is dimethylsulfoxide.

7. The system, according to claim 1 wherein said monomeric amino-aromatic compound is in a range of one to five per cent solution in said organic polar solvent.

8. The system, according to claim 1, wherein said working electrode includes submicron particles.

9. The system, according to claim 1, wherein said working electrode includes elemental gold deposited on carbon, wherein the gold is of average thickness less than one nanometer.

10. The system, according to claim 1, wherein said working electrode includes carbon paper.

11. The system, according to claim 1, further comprising,
   (b) an electrolyte for dissolving the nitro-aromatic compounds;

wherein said electrolyte is a mixed solvent including water and an organic solvent.

12. The system, according to claim 11, further comprising
(c) a mechanism for inputting air suspected to include the nitro-aromatic compounds, into said electrolyte in order to dissolve the nitro-aromatic compounds in said electrolyte.

13. The system, according to claim 11, wherein said organic solvent is selected from the group consisting of aprotonic solvents, and organic dipolar solvents.

14. The system, according to claim 11, wherein said organic solvent is selected from the group consisting of dimethylformamide, acetonitrile, propylene carbonate.

15. The system, according to claim 11, wherein said organic solvent is selected from the group consisting of ethanol, propanol, ethylene-glycol, and propylene-glycol.

16. The system, according to claim 11, wherein said electrolyte has a pH greater than 8.

17. The system, according to claim 11, wherein said electrolyte has a pH greater than 7.

18. A system for electrochemical assay of nitro-aromatic compounds, comprising:
(a) a working electrode having a surface modified by a monomeric amino-aromatic compound by treatment thereof with said monomeric amino-aromatic compound dissolved in an organic polar solvent; and
(b) an electrolyte for dissolving the nitro-aromatic compounds;
wherein said electrolyte is a mixed solvent including a water buffer of pH greater than 8, ethanol and acetonitrile.

* * * * *